US008663870B2

(12) United States Patent
Fukushima et al.

(10) Patent No.: US 8,663,870 B2
(45) Date of Patent: Mar. 4, 2014

(54) ELECTROCHEMICAL DEVICE COMPRISING LINKED BONDED BODIES

(75) Inventors: Kazuaki Fukushima, Kanagawa (JP); Shuji Goto, Kanagawa (JP); Sayaka Nanjo, Kanagawa (JP); Tetsuro Kusamoto, Kanagawa (JP)

(73) Assignee: Sony Corporation, Tokyo (JP)

( * ) Notice: Subject to any disclaimer, the term of this patent is extended or adjusted under 35 U.S.C. 154(b) by 748 days.

(21) Appl. No.: 12/447,334

(22) PCT Filed: Oct. 18, 2007

(86) PCT No.: PCT/JP2007/070316
§ 371 (c)(1),
(2), (4) Date: Apr. 27, 2009

(87) PCT Pub. No.: WO2008/050663
PCT Pub. Date: May 2, 2008

(65) Prior Publication Data
US 2010/0068562 A1      Mar. 18, 2010

(30) Foreign Application Priority Data
Oct. 27, 2006 (JP) ................. 2006-292734

(51) Int. Cl.
*H01M 2/08* (2006.01)

(52) U.S. Cl.
USPC ...................................................... 429/510

(58) Field of Classification Search
None
See application file for complete search history.

(56) References Cited

U.S. PATENT DOCUMENTS

2004/0086762 A1* 5/2004 Maeda et al. .................... 429/32
2004/0209145 A1* 10/2004 Mizukoshi et al. .............. 429/34
2005/0026026 A1* 2/2005 Yen et al. ........................ 429/36

FOREIGN PATENT DOCUMENTS

| EP | 1134830 | 9/2001 |
|---|---|---|
| JP | 9-289029 | 11/1997 |
| JP | 2002-56855 | 2/2002 |
| JP | 2003-197225 | 7/2003 |
| JP | 2005-50817 | 2/2008 |
| WO | 2005/038974 | 4/2005 |

OTHER PUBLICATIONS

International Search Report dated Jan. 29, 2008. "Function chemistry of electron and ion vol. 4: All about Polymer Electrolyte Fuel Cell," Edited by Hiroyuki Uchida and three authors, NTS Inc., 2003, pp. 143-145.
Japanese Office Action issued May 29, 2012, for corresponding Japanese Appln. No. 2006-292734.

* cited by examiner

*Primary Examiner* — Barbara Gilliam
*Assistant Examiner* — Stephan Essex
(74) *Attorney, Agent, or Firm* — K&L Gates LLP

(57) ABSTRACT

An electrochemical device capable of improving arrangement efficiency of bonded bodies and securing favorable sealing characteristics is provided. An electrolyte membrane 11 has a reaction region 11A sandwiched between a fuel electrode 12 and an oxygen electrode 13 and a peripheral region 11B exposed from between the fuel electrode 12 and the oxygen electrode 13. A connection member 20 has a bent section 23 between two flat sections 21 and 22. Since an adhesive layer 14 is provided in the peripheral section 11B of the electrolyte membrane 11, and the bent section 23 of the connection member 20 is bonded to the adhesive layer 14, arrangement efficiency of a bonded body 10 is improved, and favorable sealing characteristics are secured. The adhesive layer 14 has a structure in which a first contact layer having high adhesion to the electrolyte membrane 11, a barrier layer, a strength retention layer, and a second contact layer having high adhesion to the connection member 20 are sequentially laminated. Since a connection-member-side adhesive layer is provided on the bent section 23 of the connection member 20, adhesion strength can be further improved.

8 Claims, 9 Drawing Sheets

THERMAL COMPRESSION BOND

THERMAL COMPRESSION BOND

THERMAL COMPRESSION
BOND

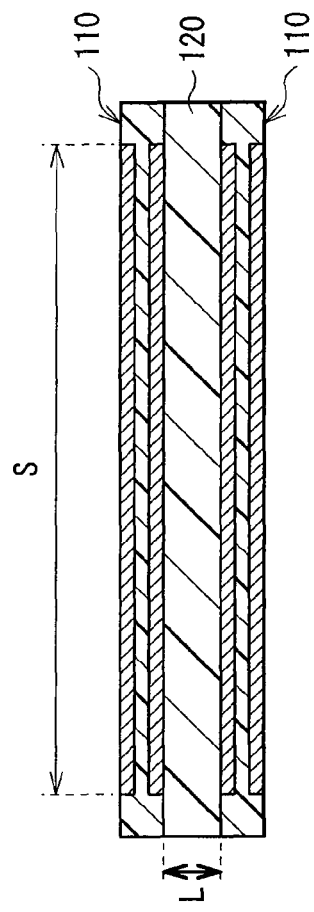
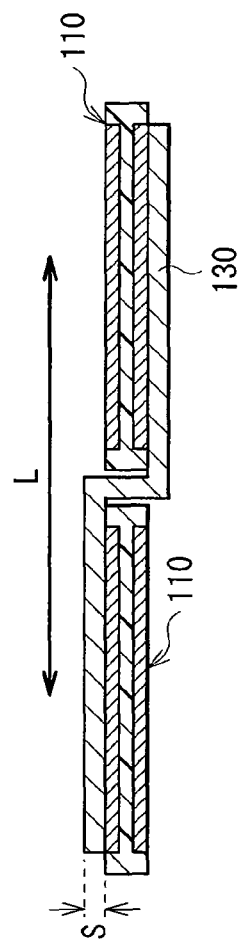
FIG. 13 (A)
FIG. 13 (B)

ELECTROCHEMICAL DEVICE COMPRISING LINKED BONDED BODIES

CROSS REFERENCE TO RELATED APPLICATIONS

The present application claims priority to Japanese Patent Document No. 2006-292734filed on Oct. 27,2006, the disclosure of which is herein incorporated by reference.

BACKGROUND

The present invention relates to an electrochemical device linking a plurality of bonded bodies in which a pair of electrodes are oppositely arranged with an electrolyte membrane in between, and particularly to an electrochemical device suitable for a fuel cell, a fuel sensor and the like.

Currently, various primary batteries and secondary batteries are used as an electric source of electronic devices. As one of indicators exhibiting characteristics of these batteries, there is an energy density. The energy density is an energy cumulative amount per unit mass of a battery.

As miniaturization and high performance of the electronic devices have been developed in recent years, a high capacity and a high output of the electric source, in particular, the high capacity of the electric source is increasingly necessitated. Thus, it has been hard to supply a sufficient energy to drive the electronic devices with the use of the conventional primary batteries and the conventional secondary batteries. Therefore, it is urgently needed to develop a battery having a higher energy density. Fuel cells attract attention as one of candidates having a higher energy density.

The fuel cell has a structure in which an electrolyte is arranged between an anode (fuel electrode) and a cathode (oxygen electrode). A fuel is supplied to the fuel electrode, and air or oxygen is supplied to the oxygen electrode. This results in redox reaction in which the fuel is oxidized by oxygen in the fuel electrode and the oxygen electrode, and part of chemical energy of the fuel is converted to electric energy and extracted.

Various types of fuel cells have been already proposed and experimentally produced, and part thereof is practically used. These fuel cells are categorized into an Alkaline Fuel Cell (AFC), a Phosphoric Acid Fuel Cell (PAFC), a Molten Carbonate Fuel Cell (MCFC), a Solid Electrolyte Fuel Cell (SOFC), a Polymer Electrolyte Fuel Cell (PEFC) and the like according to the electrolyte used.

FIG. 12 illustrates a structure of a conventional PEFC. The PEFC has a bonded body (MEA; Membrane Electrolyte Assembly) 110 in which a fuel electrode 112 and an oxygen electrode 113 are arranged with an electrolyte membrane 111 composed of a solid polymer electrolyte in between. A unit in which the bonded body 110 is sandwiched between separators (not illustrated) configures one unit cell.

A voltage capable of being extracted from the one unit cell is about 0.3 V to 0.8 V, and this voltage is not enough to be used singly. Therefore, in general, a fuel cell stack in which a plurality of unit cells are stacked is used. Meanwhile, for the use of mobile devices, a thin structure is preferred, and thus it is often the case that a plane stacked structure in which a plurality of unit cells are two-dimensionally arranged in line or in a plurality of lines, and such a plurality of unit cells are electrically connected in series is adopted.

In the two-dimensionally arranged bonded bodies 110, the electron transfer distance between adjacent two bonded bodies 110 is larger than that in vertically stacked bonded bodies. Thus, the arrangement and the current collection structure of the bonded bodies 110 are important to decrease resistance of all cells. That is, as illustrated in FIG. 13(A), in the case where the bonded bodies 110 are vertically stacked with a separator 120 in between, average transfer distance L is small and electron transfer cross-sectional area S is large, and thus electric resistance generated in the separator 120 can be kept small, resulting in an advantageous structure for flowing a large current. Meanwhile, as illustrated in FIG. 13(B), in the case where the bonded bodies 110 are two-dimensionally arranged by linking the bonded bodies 110 by a connection plate 130, by contraries, the average transfer distance L is large and the electron transfer cross-sectional area S is small, resulting in a disadvantageous structure for extracting a large current (for example, refer to Non Patent Document 1).

Conventionally, for example, the following structure has been proposed. In the structure, electricity generated in a unit cell is collected by using a Z-shaped connection plate, and adjacent unit cells are electrically connected in series, and thereby the electron transfer distance is shortened (for example, refer to Patent Document 1).

Non Patent Document 1: "Function chemistry of electron and ion Vol. 4: All about Polymer Electrolyte Fuel Cell," Edited by Hiroyuki Uchida and three authors, NTS Inc., 2003, pp. 143-145)

Patent Document 1: Japanese Unexamined Patent Application Publication No. 2002-56855

SUMMARY in the conventional structure, however, there has been a problem that since the distance between bonded bodies is large, the electrode area to the entire fuel cell is small, and the arrangement efficiency of the bonded bodies is lowered. This is because when the Z-shaped connection plate is provided, it is necessary to provide sealing between an end of the bonded body and the Z-shaped connection plate and provide sealing at the outer peripheral section of the entire fuel cell.

The sealing between the bonded body and the Z-shaped connection plate has been provided by physically adhering a sealing material such as PPS (polyphenylene sulfide) and silicone rubber sandwiching an electrolyte membrane to the Z-shaped connection plate by a fastening screw or the like. Thus, there has been a problem that the Z-shaped connection plate needs strength so that the Z-shaped connection plate can resist deformation due to tightening the screw or the like, so the thickness of the Z-shaped connection plate is needed to be thick, and it is hard to obtain a thin device. Further, it is hard to secure sufficient sealing characteristics by using a small number of fastening screws. In practice, it is necessary to fill in a sealing member between the bonded body and the Z-shaped connection plate, and it is often the case that the process are complicated.

In view of the foregoing problems, it is an object of the present invention to provide an electrochemical device capable of improving arrangement efficiency of bonded bodies and securing favorable sealing characteristics.

In the electrochemical device according to the present invention, bonded bodies in which a pair of electrodes are oppositely arranged with an electrolyte membrane in between are linked in the in-plane direction by a conductive connection member. The electrolyte membrane has a reaction region sandwiched between the pair of electrodes and a peripheral region that is exposed from the pair of electrodes and that is provided with an adhesive layer. The connection member has two flat sections and a bent section provided between the two flat sections. The respective two flat sections are contacted with one of the pair of electrodes of adjacent bonded bodies. The bent section is bonded to the adhesive layer.

According to the electrochemical device of the present invention, the adhesive layer is provided in the peripheral region of the electrolyte membrane, and the adhesive layer is adhered to the bent section of the connection member. Thus, the electrolyte membrane and the connection member are more tightly adhered by chemical adhesion, and favorable sealing characteristics can be secured. Therefore, differently from the conventional art, it is not necessary to fill in a sealing member between the bonded body and the connection member, the electrode area in the entire fuel cell can be increased, and arrangement efficiency of the bonded bodies can be improved.

Additional features and advantages of the present application are described in, and will be apparent from, the following Detailed Description and the Figures.

BRIEF DESCRIPTION OF THE FIGURES

FIG. 13 are cross sectional views for explaining a vertical stacked structure and a plane stacked structure by comparison.

DETAILED DESCRIPTION

An embodiment of the present invention will be hereinafter described in detail.

Figure 1:
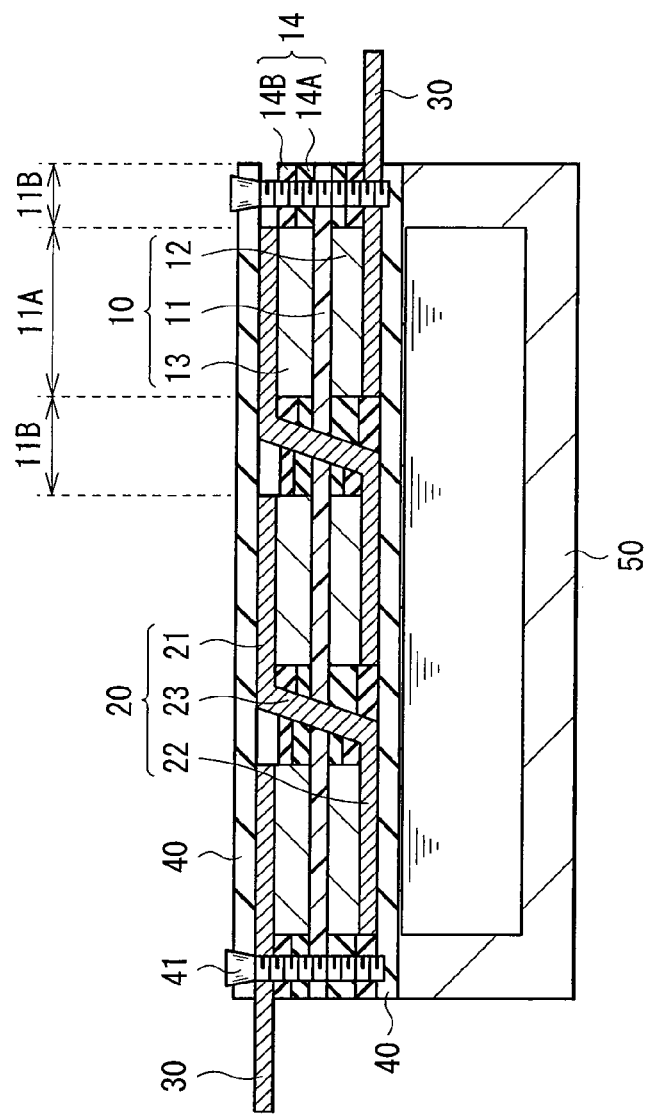
FIG. 1 is a cross sectional view illustrating a structure of a fuel cell as an electrochemical device according to an embodiment of the present invention.
Figure 2:
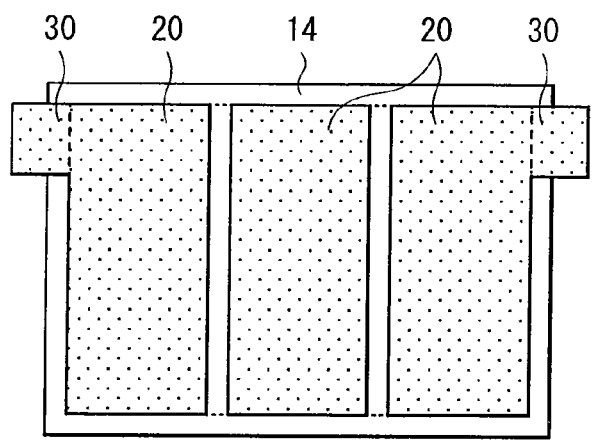
FIG. 2 is a plan view illustrating a structure viewed from an oxide electrode 13 side of the fuel cell illustrated in FIG. 1.

FIG. 1 and FIG. 2 illustrate a structure of a fuel cell as an electrochemical device according to an embodiment of the present invention. The fuel cell is a Direct Methanol Fuel Cell (DMFC) used for, for example, a mobile device such as a mobile phone and a PDA (Personal Digital Assistant) or a notebook PC (Personal Computer). The fuel cell has a plane stacked structure in which a plurality of (for example, three) bonded bodies 10 are linked in the in-plane direction by a conductive connection member 20. A terminal 30 is attached to the both endmost bonded bodies 10. On both faces of the linked bonded bodies 10, a pair of insulating plates 40 are fixed by a fastening screw 41. On the outer side of one of the insulating plates 40, a fuel supply system 50 is provided. In FIG. 2, the insulating plate 40 is omitted.

Figure 3:
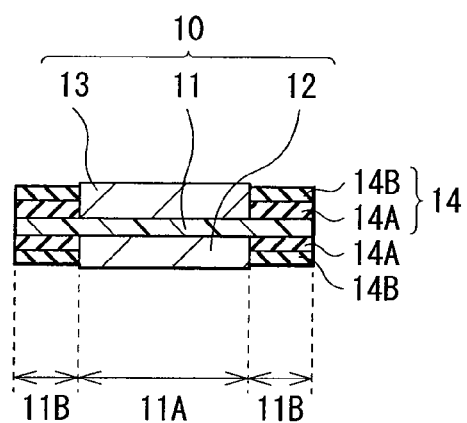
FIG. 3 is a cross sectional view illustrating a structure of the bonded body illustrated in FIG. 1.

As illustrated in FIG. 3, the bonded body 10 has a fuel electrode 12 and an oxygen electrode 13 that are oppositely arranged with an electrolyte membrane 11 in between.

The electrolyte membrane 11 has a reaction region 11A sandwiched between the fuel electrode 12 and the oxygen electrode 13 and a peripheral region 11B exposed from between the fuel electrode 12 and the oxygen electrode 13. The electrolyte membrane 11 is made of, for example, a proton conductive material having a sulfonic acid group ($-SO_3H$). As the proton conductive material, a polyperfluoroalkyl sulfonic acid proton conductive material (for example, "Nafion (registered trademark) produced by DuPont), a hydrocarbon proton conductive material such as polyimide sulfonic acid, a fullerene proton conductive material and the like are included.

The fuel electrode 12 and the oxygen electrode 13 have a structure in which, for example, a catalyst layer containing a catalyst such as platinum (Pt) and ruthenium (Ru) is formed on a current collector made of, for example, a carbon paper or the like. The catalyst layer is made of, for example, a layer in which a support substance such as carbon black supporting the catalyst is dispersed in the polyperfluoroalkyl sulfonic acid proton conductive material.

Figure 4:
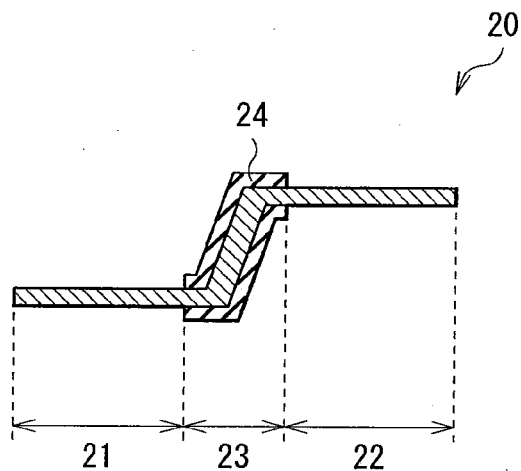
FIG. 4 is a cross sectional view illustrating a structure of the connection member illustrated in FIG. 1.

As illustrated in FIG. 4, the connection member 20 has a bent section 23 between two flat sections 21 and 22. The flat section 21 is contacted with the fuel electrode 12 of one bonded body 10, and the flat section 22 is contacted with the oxygen electrode 13 of another bonded body 10 adjacent to the foregoing one bonded body 10. Thereby, the connection member 20 electrically connects the two adjacent bonded bodies 10 in series, and also has a function as a current collector to collect electricity generated in each bonded body 10. Such a connection member 20 has a thickness of 150 μm, for example, and is made of copper (Cu), nickel (Ni), titanium (Ti), or stainless steel (SUS), and may be plated by gold (Au), platinum (Pt) or the like. Further, the connection member 20 has an aperture (not illustrated) to respectively supply a fuel and air to the fuel electrode 12 and the oxygen electrode 13, and is made of, for example, a mesh such as an expanded metal, a punching metal or the like. The bent section 23 may be previously bent adjusting to the thickness of the bonded body 10. Otherwise, in the case where the connection member 20 is made of a flexible material such as a mesh having a thickness of 200 μm or less, the bent section 23 may be formed by being bent in the manufacturing step.

Further, in this embodiment, an adhesive layer 14 is provided in the peripheral region 11B of the electrolyte membrane 11. The bent section 23 of the connection member 20 is bonded to the adhesive layer 14. Thereby, in this fuel cell, favorable sealing characteristics can be secured while improving arrangement efficiency of the bonded bodies 10.

The adhesive layer 14 has, for example, a structure in which a first contact layer 14A and a second contact layer 14B are laminated sequentially from the electrolyte membrane 11 side.

The first contact layer 14A is for obtaining adhesion to the electrolyte membrane 11. The first contact layer 14A has, for example, a thickness of 50 μm, and is made of a resin having high adhesiveness to the electrolyte membrane 11, specifically a resin obtained by modifying polyethylene, polypropylene or the like by an acid, an acid anhydride, an acid ester, metallocene, a hydroxyl group or the like; or a resin having, as a functional group, a basic substituent group such as imidazole, pyridine, and amine capable of being bonded to the sulfonic acid group of the electrolyte membrane 11 by interaction on the surface thereof. As a component material of the first contact layer 14A, for example, polyvinyl alcohol or a copolymer thereof is included.

The second contact layer 14B is for obtaining favorable bonding to the connection member 20. The second contact layer 14B has, for example, a thickness of 10 μm, and is made of a resin having high adhesion and high heat sealing characteristics to the metal composing the connection member 20, specifically a resin obtained by modifying polyethylene, polypropylene or the like by an acid, an acid anhydride, an acid ester, metallocene, a hydroxyl group or the like.

Figure 5:
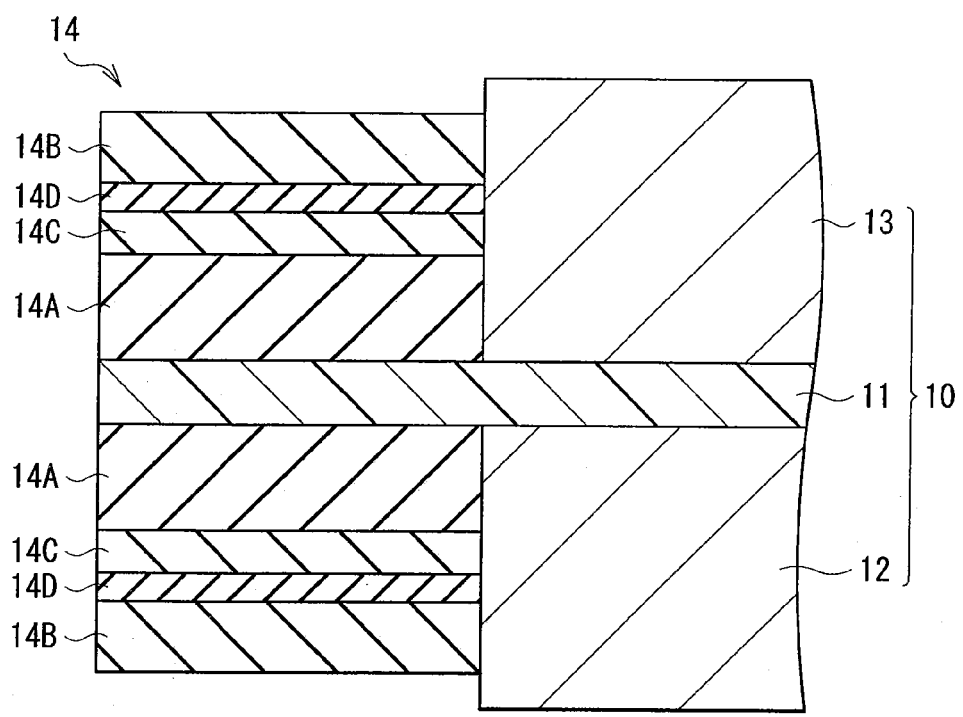
FIG. 5 is a cross sectional view illustrating a structure of the adhesive layer illustrated in FIG. 1.

Further, as illustrated in FIG. 5, the adhesive layer 14 preferably has a barrier layer 14C and a strength retention layer 14D between the first contact layer 14A and the second contact layer 14B.

The barrier layer 14C is for preventing permeation of methanol or hydrogen as a fuel and gas such as oxygen and moisture vapor. The barrier layer 14C has, for example, a thickness of 8 μm, and is made of an aluminum (Al) foil, or an inorganic evaporated layer of silicon dioxide (silica: $SiO_2$), aluminum (A), aluminum oxide (alumina) or the like.

The strength retention layer 14D is for preventing thermal deformation and melt flow in bonding to the connection member 20, and for improving mechanical strength of the bonding section to the connection member 20. The strength retention layer 14D has, for example, a thickness of 12 μm, and is made of a polyester resin such as PET (polyethylene terephthalate) or nylon.

The bent section 23 of the connection member 20 is preferably provided with a connection-member-side adhesive layer 24, since thereby the adhesion strength can be further improved. In particular, such a connection-member-side adhesive layer 24 is suitable in the case where the connection member 20 is made of a mesh such as an expanded metal and uniformly has aperture sections. The connection-member-side adhesive layer 24 is formed, for example, similarly to the second contact layer 14B.

The terminal 30 illustrated in FIG. 1 and FIG. 2 is formed similarly to the connection member 20.

The insulating plate 40 illustrated in FIG. 1 has a function to retain the physical strength of the linked bonded bodies 10, a function to secure contact between the connection member 20 and the fuel electrode 12/the oxygen electrode 13, a function to prevent electric short circuit between adjacent bonded bodies 10 and the like. The insulating plate 40 desirably has a certain strength and an aperture (not illustrated) to supply fuel to the fuel electrode 12. Such an insulating plate 40 has, for example, a thickness of 1.5 mm, and is made of aluminum (Al) provided with alumite treatment, super engineering plastic or engineering plastic such as polyphenylene sulfide and polyether ether ketone, ceramics, or a metal material such as stainless steel provided with insulating. The insulating plate 40 may be fixed by a caulking structure or adhesion by an adhesive agent, in addition to the fastening screw 41.

The fuel supply system 50 illustrated in FIG. 1 supplies a liquid fuel including methanol or the like to the fuel electrode 12 through the aperture provided in the insulating plate 40 and the connection member 20 (neither thereof illustrated). The oxygen electrode 13 is communicated with outside through the apertures provided in the insulating plate 40 and the connection member 20 (neither thereof illustrated) and is supplied with air, that is, oxygen by natural ventilation.

In addition, though not illustrated, the outer peripheral section of the fuel cell is sealed by adhering the adhesive layer 14 to the insulating plate 40 on the fuel electrode 12 side or the insulating plate 40 on the oxygen electrode 13 side to prevent the entry of air from a side face and fuel leakage. In addition, in the case where the thickness of the adhesive layer 14 is not sufficient, it is possible to address it by increasing the number of layers of the adhesive layer 14 and increasing the thickness thereof. Further, instead of the adhesive layer 14, or in addition to the adhesive layer 14, a sealing member such as silicone rubber may be provided only in the outer peripheral section.

The fuel cell can be manufactured, for example, as follows.

FIGS. 6 to 9 illustrate a method of manufacturing this fuel cell in order of steps. First, the electrolyte membrane 11 that has plane dimensions of, for example, 20 mm×40 mm and is made of the foregoing material is sandwiched between the fuel electrode 12 and the oxygen electrode 13 that have, for example, plane dimensions of 15 mm×35 mm and are made of the foregoing material. The resultant is thermally compression-bonded for 15 minutes at 130 deg C. under a pressure of 0.5 kN, for example. Thereby, the fuel electrode 12 and the oxygen electrode 13 are bonded to the electrolyte membrane 11 to form the bonded body 10. At this time, in the electrolyte membrane 11, the reaction region 11A sandwiched between the fuel electrode 12 and the oxygen electrode 13 and the peripheral region 11B exposed from between the fuel electrode 12 and the oxygen electrode 13 are formed.

Next, in the peripheral region 11B of the electrolyte membrane 11, the first contact layer 14A, the barrier layer 14C, the strength retention layer 14D, and the second contact layer 14B made of the foregoing materials are sequentially laminated to form the adhesive layer 14. The first contact layer 14A, the barrier layer 14C, the strength retention layer 14D, and the second contact layer 14B may be previously laminated by thermal bonding or dry lamination using an adhesive agent or the like before being laminated over the electrolyte membrane 11. Further, as the first contact layer 14A and the second contact layer 14B, a film-like or sheet-like resin made of the foregoing material may be used.

Further, the connection member 20 made of the foregoing material is prepared. On the bent section 23 thereof, the connection-member-side adhesive layer 24 made of the foregoing material is provided.

Figure 6A:
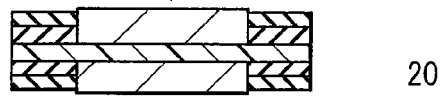
FIG. 6 are cross sectional views illustrating a method of manufacturing the fuel cell illustrated in FIG. 1 in order of steps.
Figure 6B:
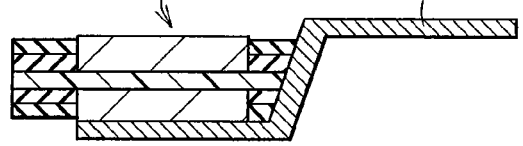
Figures 7A, 7B:
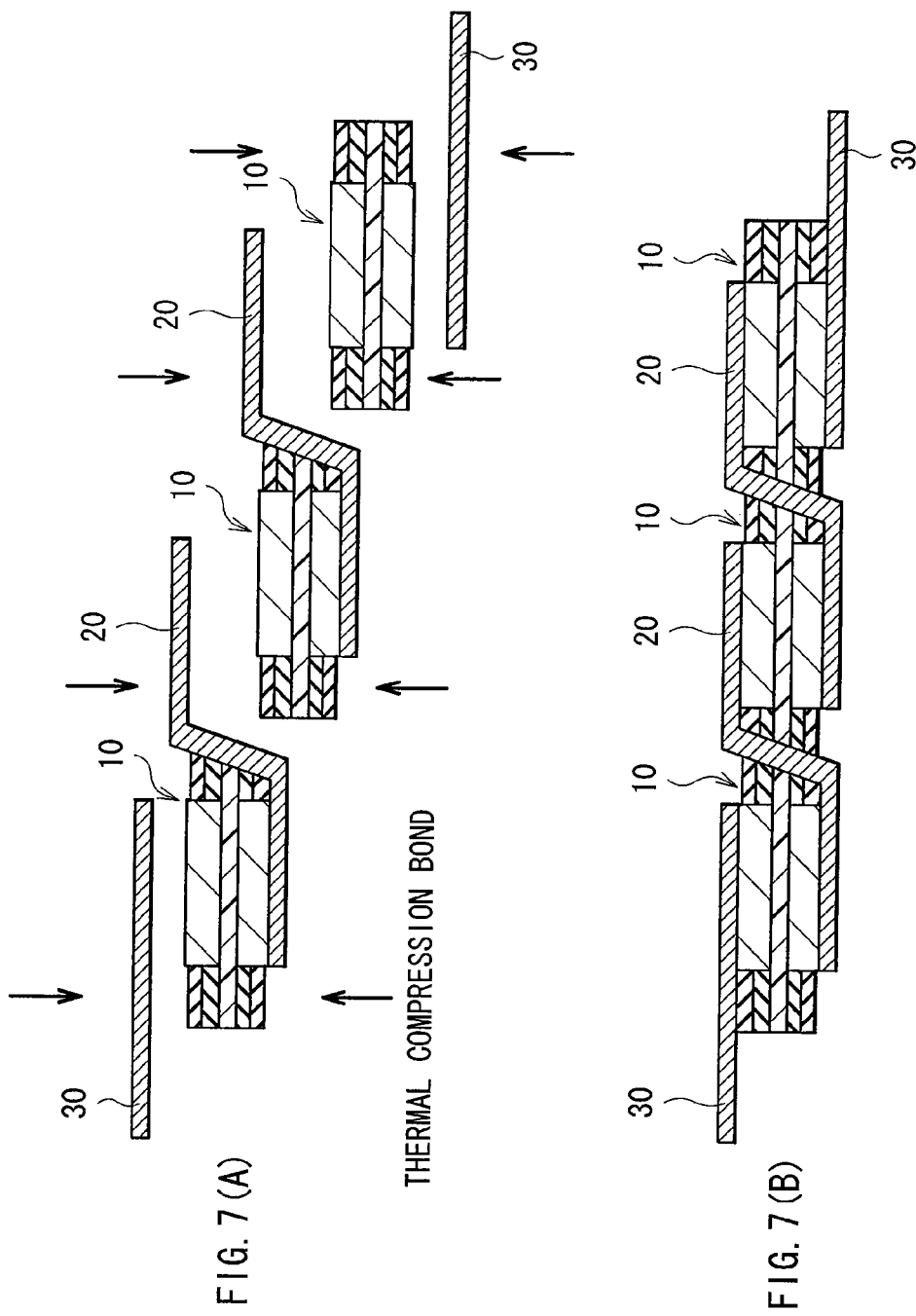
FIG. 7 are cross sectional views illustrating steps following FIG. 6.

Subsequently, as illustrated in FIG. 6(A) and FIG. 6(B), the adhesive layer 14 of the electrolyte membrane 11 is compression-bonded to the connection-member-side adhesive layer 24 of the bent section 23 of the connection member 20 for 10 seconds at 170 deg C. Similarly, as illustrated in FIG. 7(A) and FIG. 7(B), three bonded bodies 10 are linked in line by the connection member 20, and the terminal 30 is attached to the both endmost bonded bodies 10. This step can be performed by using an ultrasonic welder.

Figure 8A:
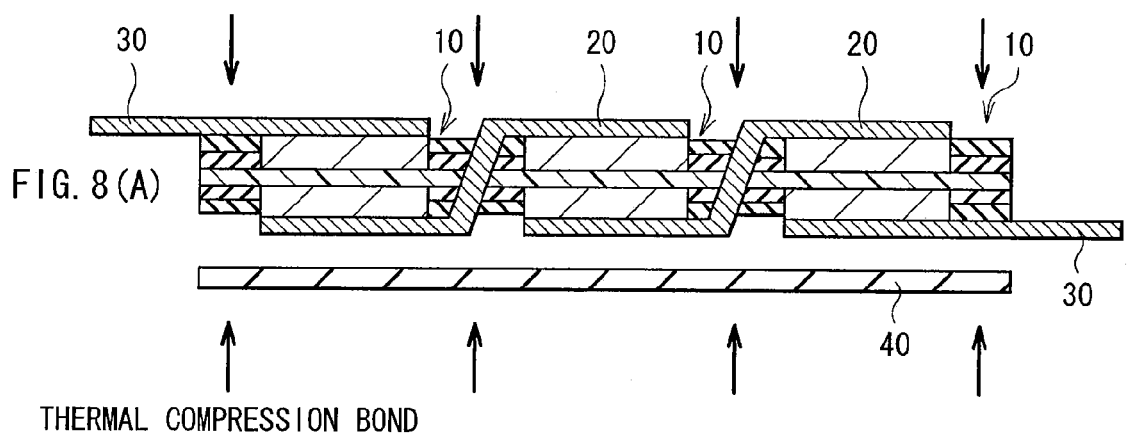
FIG. 8 are cross sectional views illustrating steps following FIG. 7.
Figure 8B:
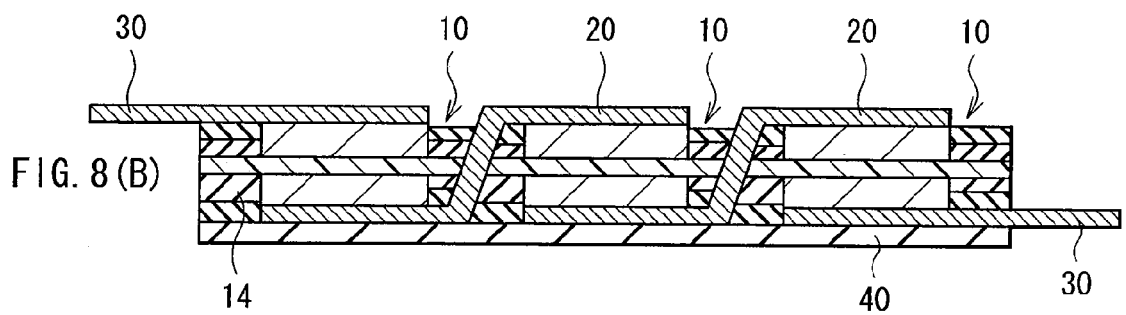
Figure 9:
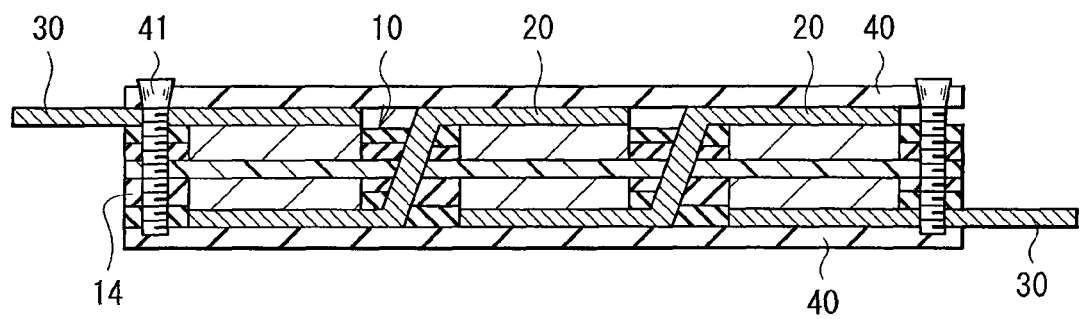
FIG. 9 is a cross sectional view illustrating a step following FIG. 8.

After that, as illustrated in FIG. 8(A) and FIG. 8(B), the insulating plate 40 is thermally compression-bonded to the fuel electrode 12 of the linked bonded bodies 10 for 30 seconds at 170 deg C., and thereby the fuel electrode 12 is shielded from the air. This step may be performed by using an ultrasonic welder. Further, as illustrated in FIG. 9, the insulating plate 40 is also arranged on the oxygen electrode 13, and the two insulating plates 40 are fixed by the fastening screw 41. Finally, the fuel supply system 50 is attached to the outer side of the insulating plate 40 on the fuel electrode 12 side. Accordingly, the fuel cell illustrated in FIG. 1 and FIG. 2 is completed. In addition, the fuel cell was actually fabricated by this manufacturing method, and the output was examined. Then, an output current of 900 mA at a voltage of 1.0 V was obtained (900 mW).

In the fuel cell, the fuel is supplied to the fuel electrode 12, and protons and electrons are generated by reaction. The protons are transferred to the oxygen electrode 13 through the electrolyte membrane 11, and are reacted with electrons and oxygen to generate water. In the fuel cell, the adhesive layer 14 is provided in the peripheral region 11B of the electrolyte membrane 11, and the adhesive layer 14 is adhered to the bent section 23 of the connection member 20. Thus, the electrolyte membrane 11 and the connection member 20 are tightly adhered by chemical adhesion. Therefore, differently from the conventional art, it is not necessary to fill in a sealing member between the bonded body and the connection member. Accordingly, the distance between the bonded bodies 10 is reduced, the bonded bodies 10 are connected in series with small electric resistance, and the output current is increased.

As described above, according to this embodiment, the adhesive layer 14 is provided in the peripheral region 11B of the electrolyte membrane 11, and the adhesive layer 14 is adhered to the bent section 23 of the connection member 20. Thus, the electrolyte membrane 11 and the connection member 20 are tightly adhered by chemical adhesion, and favorable sealing characteristics can be secured. Therefore, differently from the conventional art, it is not necessary to fill in a sealing member between the bonded body and the connection member, the electrode area in the entire fuel cell can be increased, and arrangement efficiency of the bonded bodies 10 can be improved.

In addition, in the foregoing embodiment, the description has been given of a case where the adhesive layer 14 has a structure in which the first contact layer 14A, the barrier layer 14C, the strength retention layer 14D, and the second contact layer 14B are laminated sequentially from the electrolyte membrane 11 side. However, it is enough that the adhesive layer 14 has at least the first contact layer 14A, and the barrier layer 14C, the strength retention layer 14D, and the second contact layer 14B may be provided according to needs.

Further, the lamination order of the barrier layer 14C and the strength retention layer 14D is not particularly limited. For example, it is possible that the first contact layer 14A, the strength retention layer 14D, the barrier layer 14C, and the second contact layer 14B may be laminated sequentially from the electrolyte membrane 11 side.

Further, both the barrier layer 14C and the strength retention layer 14D may be provided, or only one thereof may be provided. Further, the first contact layer 14A or the second contact layer 14B may have the function of the barrier layer 14C or the strength retention layer 14D.

(Modified Example)

Figure 10:
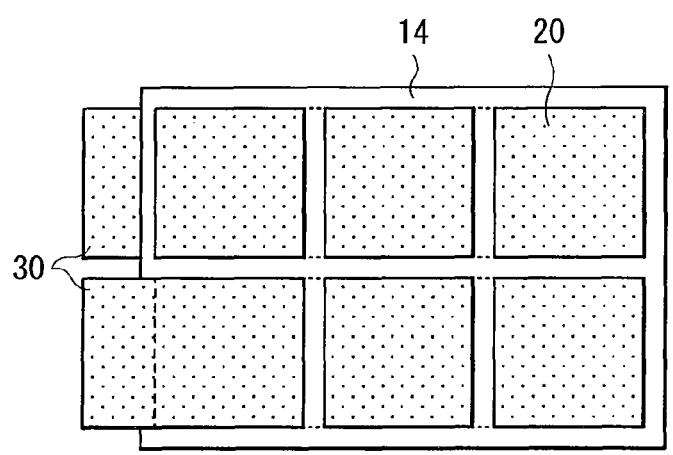
FIG. 10 is a plan view illustrating a structure viewed from the oxide electrode 13 side of a fuel cell as an electrochemical device according to a modified example of the present invention.

FIG. 10 illustrates a structure of a fuel cell as an electrochemical device according to a modified example of the present invention. The fuel cell has the same structure as that of the fuel cell described in the foregoing embodiment except that six bonded bodies 10 are arranged in a two-dimensional arrangement composed of three columns by two lines. The fuel cell according to the modified example of the present invention can be manufactured similarly to the fuel cell described in the foregoing embodiment. Therefore, the same reference symbols as those of the fuel cell described in the foregoing embodiment are affixed to the corresponding elements.

Figure 11:
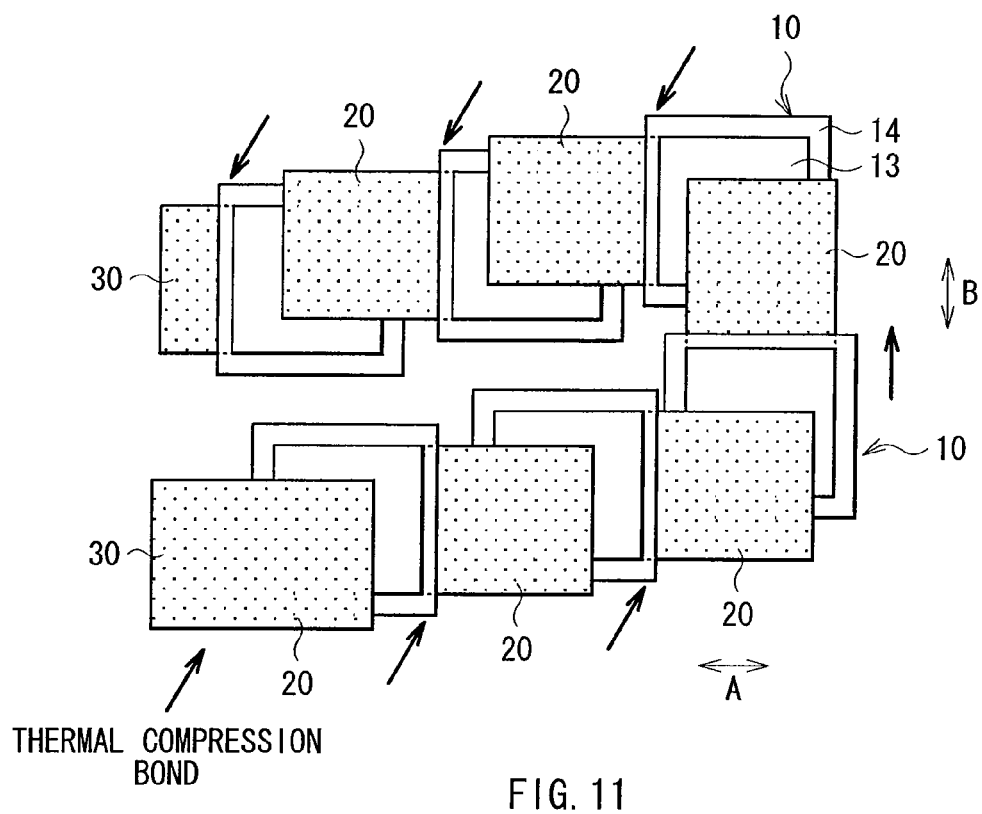
FIG. 11 is an exploded plan view of the fuel cell illustrated in FIG. 10.
Figure 12:
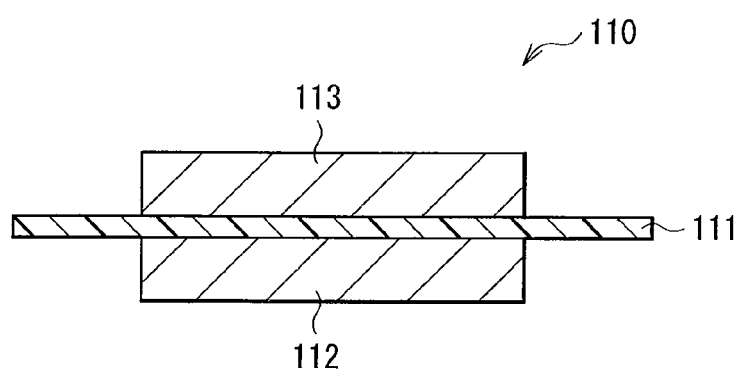
FIG. 12 is a cross sectional view illustrating a structure of a conventional fuel cell.

As illustrated in the exploded view of FIG. 11, these six bonded bodies 10 are linked in column direction B at one end in line direction A, and are linked in the line direction A at the locations other than the foregoing one end, and thereby these six bonded bodies 10 are linked in a state of so-called U-shape. Thereby, in this modified example, degree of freedom of arrangement method in the plane stacked structure is increased, and a large voltage can be extracted by using many bonded bodies 10. For example, in the case where the number of lines in the two-dimensional arrangement is increased to 3 or more, bonded bodies 10 are repeatedly linked in the column direction B at one end in one line and at the other end in the subsequent line, and are linked in a meander shape as a whole. Thereby, no matter how mach the number of bonded bodies 10 is increased, the bonded bodies 10 can be electrically connected in series. Further, the bonded bodies 10 may be linked in spirals or in whorl. In addition, six bonded bodies 10 having the fuel electrode 12 and the oxygen electrode 13 with dimensions of 15 mm×15 mm were actually fabricated, the fuel cell in which the six bonded bodies 10 were linked in a state of U-shape was actually fabricated as illustrated in FIG. 10 and FIG. 11, and the output was examined. Then, an output current of 400 mA at a voltage of 2.0 V was obtained (800 mW), and the degree of freedom of arrangement method was confirmed.

The present invention has been described with reference to the embodiment. However, the present invention is not limited to the foregoing embodiment, and various modifications may be made. For example, in the foregoing embodiment, the specific description has been given of the structures of the electrolyte membrane 11, the fuel electrode 12, and the oxygen electrode 13. However, the electrolyte membrane 11, the fuel electrode 12, and the oxygen electrode 13 may have other structure, or may be made of other material.

Further, for example, the adhesion method and the adhesion conditions such as the heating temperature, the pressure, and the time or the like are not limited to those described in the foregoing embodiment. Other adhesion method and other adhesion conditions may be adopted. For example, in the foregoing embodiment, after the adhesive layer 14 is formed in the peripheral region 11B of the electrolyte membrane 11, the adhesive layer 14 is adhered to the connection member 20. However, it is possible that after the connection member 20 and the adhesive layer 14 are adhered to each other, the adhesive layer 14 is thermally adhered to the electrolyte membrane 11.

Further, in the foregoing embodiment, air supply to the oxygen electrode 13 is implemented by natural ventilation. However, air may be forcibly supplied by utilizing a pump or the like. In this case, instead of air, oxygen or gas containing oxygen may be supplied.

In addition, the present invention is applicable to not only the DMFC, but also other type of fuel cell such as a Polymer Electrolyte Fuel Cell using hydrogen as a fuel, a Direct Ethanol Fuel Cell, and a Dimethyl Ether Fuel Cell.

Furthermore, in the foregoing embodiment, the description has been given of the fuel cell as an electrochemical device. However, in addition to the fuel cell, the present invention is applicable to other electrochemical device such as a capacitor and a fuel sensor.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention claimed is:

1. An electrochemical device comprising linked bonded bodies in which a pair of electrodes are oppositely arranged with an electrolyte membrane in between in an in-plane direction by a conductive connection member, wherein
the electrolyte membrane has a reaction region sandwiched between the pair of electrodes, and has a peripheral region that is exposed from the pair of electrodes and that is provided with adhesive layers on opposite sides of the electrolyte membrane, and the connection member has two flat sections and a bent section provided between the two flat sections, the respective two flat sections are contacted with one of the pair of electrodes of adjacent bonded bodies, and the bent section is bonded to each of the adhesive layers, wherein each of the adhesive layers includes a first contact layer contacted with the electrolyte membrane, and a second contact layer on a side opposite to the electrolyte membrane with respect to the first contact layer, wherein the second contact layer is separate from the first contact layer; and wherein each of the adhesive layers includes a barrier layer and a strength retention layer between the first contact layer and the second contact layer, wherein the barrier layer is separate from the strength retention layer.

2. The electrochemical device according to claim 1, wherein each of the adhesive layers includes at least one of a barrier layer and a strength retention layer between the first contact layer and the second contact layer.

3. The electrochemical device according to claim 1, wherein a connection-member-side adhesive layer is provided on the bent section of the connection member, wherein the connection-member-side adhesive layer is separate from the adhesive layers.

4. The electrochemical device according to claim 1, wherein the bonded bodies are arranged in a two-dimensional arrangement composed of a plurality of lines and columns, and the connection member links the bonded bodies in column direction at one end or both ends in line direction, and links the bonded bodies in the line direction at locations other than the one end or the both ends in line direction.

5. The electrochemical device according to claim 1 wherein the electrochemical device is a fuel cell in which a fuel electrode and an oxygen electrode are oppositely arranged with the electrolyte membrane in between.

6. The electrochemical device according to claim 3, wherein the connection-member-side adhesive layer is bonded to each of the adhesive layers.

7. The electrochemical device according to claim 1, wherein the barrier layer is made of at least one of aluminum foil, an inorganic evaporated layer of silicon dioxide, an inorganic evaporated layer of aluminum, and an inorganic evaporated layer of aluminum oxide.

8. The electrochemical device according to claim 1, wherein the strength retention layer is made of at least one of a polyester resin and nylon.

* * * * *